(12) United States Patent
Worthley

(10) Patent No.: US 7,119,247 B2
(45) Date of Patent: Oct. 10, 2006

(54) DRESSING AND A METHOD FOR MAKING AND APPLYING A DRESSING

(75) Inventor: George Worthley, Wheaton, IL (US)

(73) Assignee: George Medical, LLC, Wheaton, IL (US)

(*) Notice: Subject to any disclaimer, the term of this patent is extended or adjusted under 35 U.S.C. 154(b) by 153 days.

(21) Appl. No.: 10/278,672

(22) Filed: Oct. 22, 2002

(65) Prior Publication Data
US 2004/0077984 A1 Apr. 22, 2004

(51) Int. Cl.
*A61F 13/00* (2006.01)
*A61F 15/00* (2006.01)

(52) U.S. Cl. .......................... 602/54; 602/42; 602/43; 602/59; 602/55

(58) Field of Classification Search ............ 602/41–59; 128/888, 889; 604/304–308, 290
See application file for complete search history.

(56) References Cited

U.S. PATENT DOCUMENTS

| | | | |
|---|---|---|---|
| 4,324,237 A | 4/1982 | Buttaravoli | |
| 4,534,762 A | 8/1985 | Heyer | |
| 4,669,458 A | 6/1987 | Abraham et al. | |
| 4,678,462 A | 7/1987 | Vaillancourt | |
| 4,969,880 A | 11/1990 | Zamierowski | |
| 4,995,382 A * | 2/1991 | Lang et al. .................... 602/55 |
| 5,000,741 A | 3/1991 | Kalt | |
| 5,112,313 A | 5/1992 | Sallee | |
| 5,409,472 A * | 4/1995 | Rawlings et al. ........... 604/307 |
| 5,569,207 A | 10/1996 | Gisselber et al. | |
| 5,599,289 A | 2/1997 | Castellana | |
| 5,658,629 A * | 8/1997 | Delcuve et al. ............. 428/41.3 |
| 5,738,642 A | 4/1998 | Heinecke et al. | |
| 5,885,254 A * | 3/1999 | Matyas ....................... 604/180 |
| 6,043,406 A * | 3/2000 | Sessions et al. .............. 602/41 |
| 6,124,520 A * | 9/2000 | Roberts ....................... 602/54 |
| 6,149,614 A | 11/2000 | Dunshee et al. | |
| 6,548,727 B1 * | 4/2003 | Swenson ..................... 602/41 |
| 2002/0169405 A1* | 11/2002 | Roberts ....................... 602/43 |
| 2003/0125685 A1* | 7/2003 | Swenson ................... 604/369 |

\* cited by examiner

*Primary Examiner*—Henry Bennett
*Assistant Examiner*—Kari Petrik
(74) *Attorney, Agent, or Firm*—Patents & TMS, P.C.

(57) ABSTRACT

A film dressing for catheter sites and a method for applying and making such a dressing are provided. Preferably, the film dressing has a foam layer. A moisture vapor semi-permeable film may be secured to the foam layer. A window in the foam layer allows for viewing of the catheter site. The moisture vapor semi-permeable film may be coated with an adhesive for application to a catheter site. The adhesive may vary in strength and pattern. The dressing may further have a liner coated with silicone for use in protection of the semi-permeable film. A label may be removable attached to the silicone coated liner. The dressing may further have additional foam pieces for use in the application of the dressing to a patient. The dressing may have different colors indicating, for example, the strength of the adhesive used with the dressing.

4 Claims, 5 Drawing Sheets

DRESSING AND A METHOD FOR MAKING AND APPLYING A DRESSING

BACKGROUND OF THE INVENTION

The present invention generally relates to a film dressing for intravenous catheter sites as well as a method for making and applying such a dressing. More specifically, the present invention relates to a film dressing having a top foam layer having a window exposing a moisture vapor semi-permeable film. The moisture vapor semi-permeable film may be coated with an adhesive. The dressing may further have a liner for protection of the dressing and for use in the application of the dressing to a patient. The dressing of the present invention may be placed in a pouch and may be sterilized for use on a patient.

It is, of course, generally known to use film dressings for the treatment and/or covering of wounds or intravenous catheter sites. Catheter dressings that are self adherent are known. Such dressings are generally in the form of a transparent polyurethane film having an adhesive and a liner. Other known dressings include a fabric layer having an adhesive side, a sheet of film closing a window in the fabric layer, and an absorbent fiber layer on the adhesive side of the fabric tape layer. Known dressings generally have a cut in the fabric layer extending beyond the periphery of the absorbent fiber layer for receiving a catheter tube. The fabric layer seals the window dressing from contamination around the catheter tube.

A problem associated with these dressings includes adhesive that may damage the skin of the patient. For example, the adhesive of the known dressings may damage the skin or cause pain to the patient when the adhesive is applied and/or removed. More specifically, the elderly, newborns, burn patients, or other patients with sensitive, frail or damaged skin may suffer pain or otherwise be further harmed by the use of the adhesive on the dressing.

Further, dressings that do not use adhesive to secure the dressing to the skin of the patient are known. For example, a dressing is designed with bands that wrap around the patient adjacent the catheter site. The bands attach to each other using hook and loop fasteners. Adhesive is used to secure the catheter tubing against the bands and not the skin of the patient. Another known dressing has wings that wrap around the patient adjacent the catheter site. The wings are secured to a base unit with adhesive. However, these dressings are costly to manufacture, may have a tourniquet effect, do not allow for a clear view of the catheter insertion site and are not as easy to use as self-adherent dressings.

A need, therefore, exists for a film dressing for intravenous catheter sites and a method for making and a method for applying such a dressing that is easy and safe to use with patients having sensitive skin, maintains adherence to the skin and/or catheter and protects the wound from exposure to harmful environmental conditions, such as bacteria or the like.

SUMMARY OF THE INVENTION

The present invention generally relates to a film dressing to cover a catheter site and a method for applying such a dressing. Preferably, the film dressing has a foam layer and a moisture vapor semi-permeable film secured to the foam layer. The moisture vapor semi-permeable film may be coated with any one of a number of different adhesives. The dressing may further have additional foam pieces for use in the application of the dressing to a patient and the foam layer and foam pieces may have different colors indicating the strength of the adhesive.

To this end, in an embodiment of the present invention, a dressing is provided having a semi-permeable film having a top side and a bottom side, a layer secured to the top side of the semi-permeable film, a first adhesive on the bottom side of the semi-permeable film and a second adhesive on the bottom side of the layer. The second adhesive has an adhesive strength greater than an adhesive strength of the first adhesive.

In an embodiment, the dressing has a pattern associated with the first adhesive wherein the pattern allows vapor transmission.

In an embodiment, the layer is foam.

In an embodiment, the dressing has a liner attached to the first adhesive and the second adhesive.

In an embodiment, the dressing has a piece of foam having a bottom side wherein the bottom side of the piece of foam is coated with the second adhesive.

In an embodiment, the dressing has a color associated with the layer wherein the color is indicative of the adhesive strength of the second adhesive.

In an embodiment, the dressing has a window in the layer wherein the window forms an opening in the layer.

In another embodiment of the present invention, a dressing is provided having a semi-permeable film having an adhesive, a layer secured to the semi-permeable film and a liner secured to the layer. The layer has an adhesive and the liner has a top side and a bottom side. The top side and the bottom side of the liner are coated with silicone.

In an embodiment, the dressing has a label removably attached to the liner.

In an embodiment, the liner is secured to the semi-permeable film.

In an embodiment, the dressing has a piece of foam having an adhesive wherein the piece of foam is removably attached to the liner.

In another embodiment of the present invention, a method for applying one of a plurality of dressings to a patient is provided. Each one of the plurality of dressings has a layer, a color associated with the layer, a semi-permeable film, an adhesive and a liner. The method comprises the steps of: choosing a dressing based on the color associated with the layer wherein the color indicates an adhesive strength of the adhesive; providing a piece of foam removably attached to the liner; exposing the dressing by removing the liner; placing the exposed portion of the dressing on the patient such that the adhesive adheres to the patient; and securing the dressing on the patient with the piece of foam.

In an embodiment, the method for applying one of a plurality of dressings to a patient further comprises the steps of removing the liner and placing the exposed portion of the dressing on the patient.

In an embodiment, the method for applying one of a plurality of dressings to a patient further comprises the steps of providing a label on the dressing and writing information on the label.

In an embodiment, the method for applying one of a plurality of dressings to a patient further comprises the step of removing the label from the dressing.

In an embodiment, the method for applying one of a plurality of dressings to a patient further comprises the steps of providing foam coated on one side with a first adhesive; securing the foam to a semi-permeable film coated with a second adhesive; and forming a liner on the foam wherein the liner has a top side and a back side wherein the top side and the back side are coated with silicone.

In an embodiment, the method for applying one of a plurality of dressings to a patient further comprises the first adhesive having an adhesive strength stronger than an adhesive strength of the second adhesive.

In an embodiment, the method for applying one of a plurality of dressings to a patient further comprises the foam having a color indicative of an adhesive strength of the first adhesive.

In an embodiment, the method for applying one of a plurality of dressings to a patient further comprises the step of forming the liner on the semi-permeable film.

In an embodiment, the method for applying one of a plurality of dressings to a patient further comprises the steps of cutting pieces of foam from the foam and applying the foam pieces to the liner.

In an embodiment, the method for applying one of a plurality of dressings to a patient further comprises the step of cutting a window through the foam.

In another embodiment of the present invention, a dressing is provided having a semi-permeable film having a top side and a bottom side, a first adhesive on the bottom side of the semi-permeable film, a foam layer having a bottom side, a second adhesive on the bottom side of the foam layer and a color associated with the foam layer. The first adhesive allows vapor transmission. The foam layer is secured to the top side of the semi-permeable film. The color associated with the foam layer is indicative of the adhesive strength of the second adhesive.

In an embodiment, the dressing has a pattern associated with the first adhesive wherein variation in the pattern is indicative of a rate of the vapor transmission of the first adhesive through the semi-permeable film.

It is, therefore, an advantage of the present invention to provide a dressing and a method for making and applying such a dressing to cover a wound and/or a catheter site.

Another advantage of the present invention is to provide a dressing and a method for making and applying such a dressing that promotes moist wound healing.

Another advantage of the present invention is to provide a dressing and a method for making and applying such a dressing wherein the dressing is easy to use and inexpensive to manufacture.

Further, an advantage of the present invention is to provide a dressing and a method for making and applying such a dressing wherein the dressing is securely adhered to a patient and/or catheter.

A still further advantage of the present invention is to provide a dressing and a method for making and applying such a dressing wherein the dressing has an adhesive that varies in strength.

Another advantage of the present invention is to provide a dressing and a method for making and applying such a dressing wherein the dressing may have different colors to indicate a strength of the adhesive.

Yet another advantage of the present invention is to provide a dressing and a method for making and applying such a dressing wherein a label on the dressing provides patient identification and/or information.

Another advantage of the present invention is to provide a dressing and a method for making and applying such a dressing wherein the dressing maintains cleanliness of the wound and/or catheter site and protects the wound and/or catheter site from harmful environmental conditions, such as bacteria or the like.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1A:
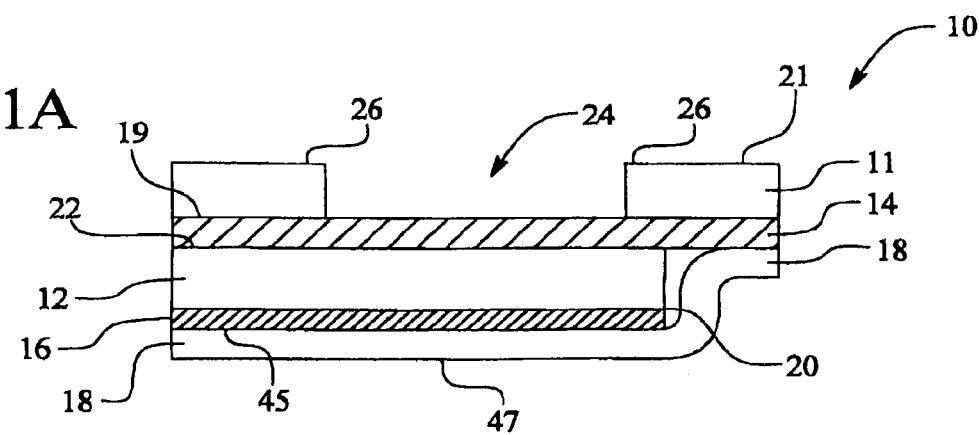
FIG. 1a is a cross-sectional view of a dressing taken generally along the line AB—AB of FIG. 2 in an embodiment of the present invention.

The present invention generally relates to a film dressing to cover a wound and/or a catheter site and a method for making and applying the same. The dressing may have a foam layer, a moisture vapor semi-permeable film and an adhesive wherein the foam layer and the semi-permeable film are secured by the adhesive. The adhesive of the film may vary in strength and the foam layer may have a color indicating the strength of the adhesive. The dressing may further have additional foam pieces for use in securing the dressing to a patient.

Referring now to the drawings wherein like numerals refer to like parts, FIGS. 1a–1d and 2 illustrate a dressing 10 of the present invention. As shown in FIGS. 1a–1d, the dressing 10 may have a number of layers. More specifically, the dressing 10 may have a foam layer 11, a semi-permeable film 12, a first adhesive layer 14, a second adhesive layer 16, and a liner 18. Preferably, the semi-permeable film 12 is transparent.

Figure 1B:
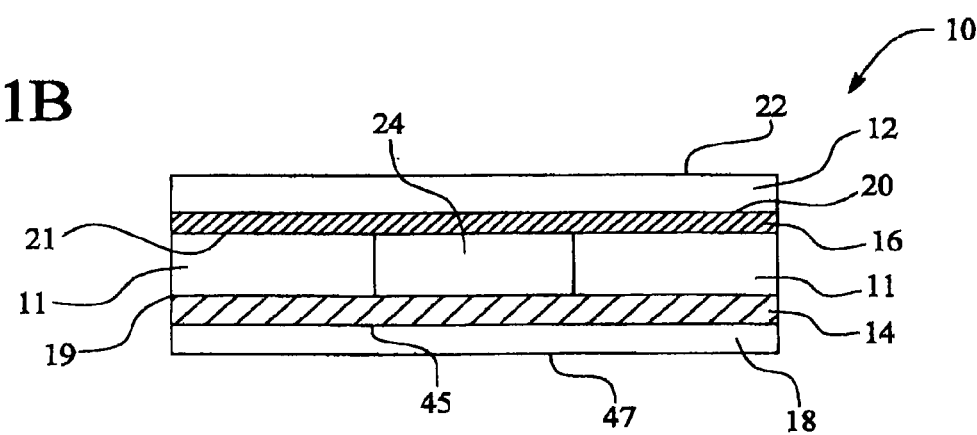
FIG. 1b is a cross-sectional view of a dressing taken generally along the line AB—AB of FIG. 2 in an embodiment of the present invention.
Figure 1C:
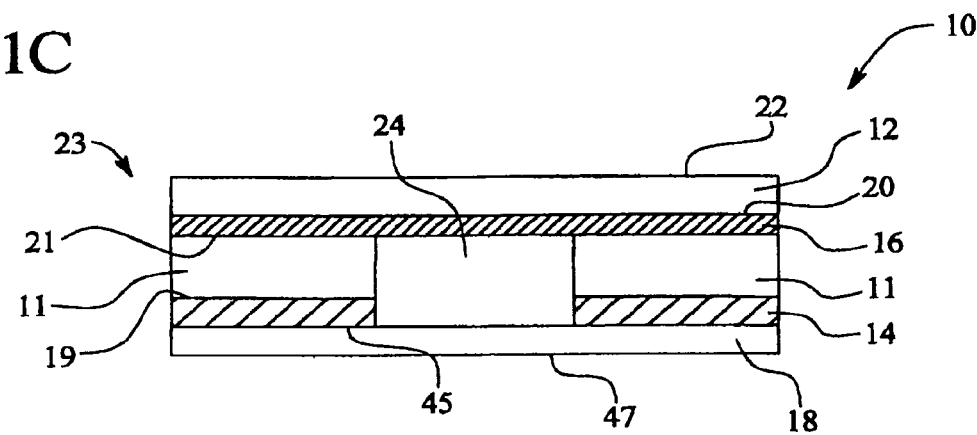
FIG. 1c is a cross-sectional view of a dressing taken generally along the line CD—CD of FIG. 2 in an embodiment of the present invention.
Figure 1D:
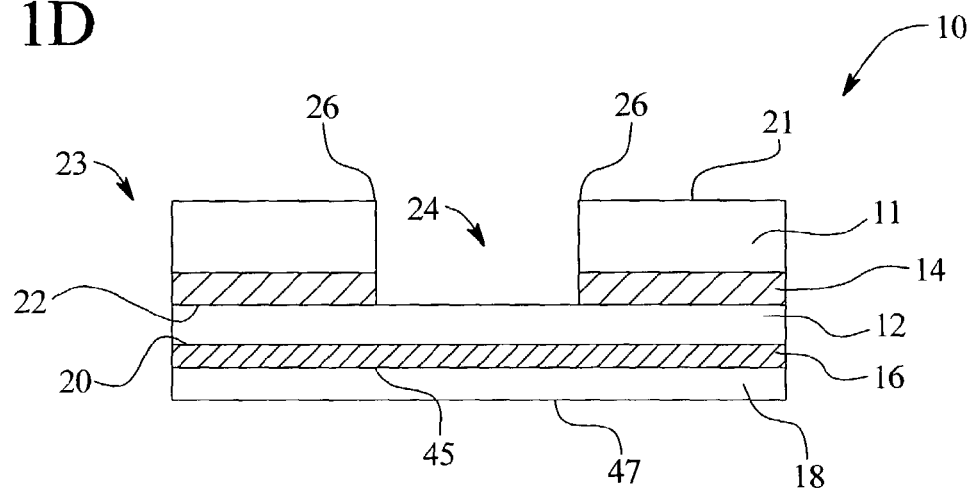
FIG. 1d is a cross-sectional view of a dressing taken generally along the line CD—CD of FIG. 2 in an embodiment of the present invention.

The foam layer 11 may have a top 21 and a bottom 19 wherein the bottom 19 of the foam layer 11 is coated with the first adhesive layer 14. The semi-permeable film 12 may have a top side 22 and a bottom side 20 opposite from the top side 22. As shown in FIGS. 1b and 1c, the semi-permeable film 12 may be coated on the bottom side 20 with the second adhesive layer 16 and the bottom side 20 of the semi-permeable film 12 may be adhesively secured to the top 21 of the foam layer 11. The liner 18 may be removably attached to the first adhesive layer 14 coated on the bottom 19 of the foam layer 11. Alternatively, as shown in FIGS. 1*a* and 1*d*, the top side 22 of the semi-permeable film 12 may be secured to the first adhesive layer 14 on the bottom 19 of the foam layer 11. The liner 18 may be removably attached to the second adhesive layer 16 coated on the bottom side 20 of the semi-permeable film 12.

Figure 1E:
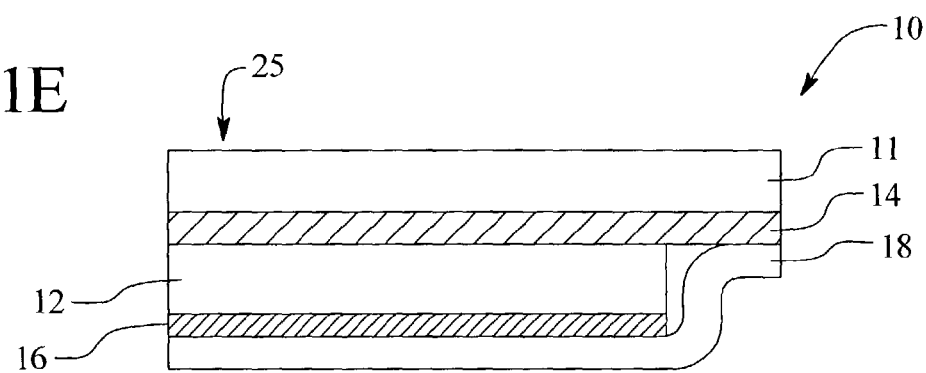
FIG. 1e is a cross-sectional view of a dressing taken generally along the line E—E of FIG. 2 in an embodiment of the present invention.
Figure 2:
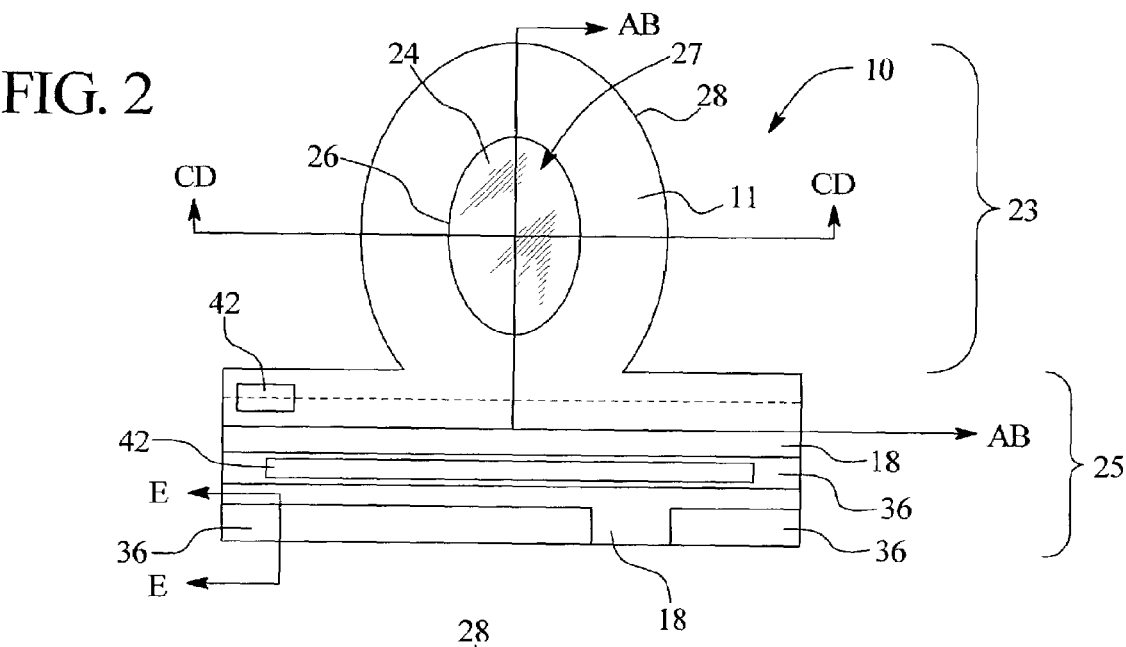
FIG. 2 is a top view of a dressing in an embodiment of the present invention.

As shown in FIGS. 1*a*–1*d* and 2, the layers of the dressing 10 including the foam layer 11, the semi-permeable film 12, the first adhesive layer 14, the second adhesive layer 16, and the liner 18 may be defined by a base 23. As shown in FIGS. 1*e* and 2, the layers of the dressing 10 including the foam layer 11, the first adhesive layer 14, and the liner 18 may be defined by a wing 25. The wing 25 may be attached to and extend from the base 23. When the dressing 10 is applied to the patient, the base 23 may be applied to the catheter site area and the wing 25 may secure the dressing 10 to the patient and/or may secure the catheter.

Referring again to FIGS. 1*a*–1*d* and 2, the semi-permeable film 12 may be constructed of polyurethane and/or may be moisture vapor permeable. Further, the semi-permeable film 12 may be transparent for viewing of the catheter insertion point on a patient. More specifically, the dressing 10 may have a window 24 cut into the foam layer 11 of the base 23. The window 24 may allow for viewing of the catheter site through the semi-permeable film 12. The window 24 cut into the foam layer 11 of the base 23 may have a perimeter 26. The foam layer 11 may substantially surround the perimeter 26 of the window 24. As a result, the foam layer 11 may frame the window 24. The window 24 may be formed by cutting an opening 27 in the foam layer 11 around the perimeter 26.

Figure 3:
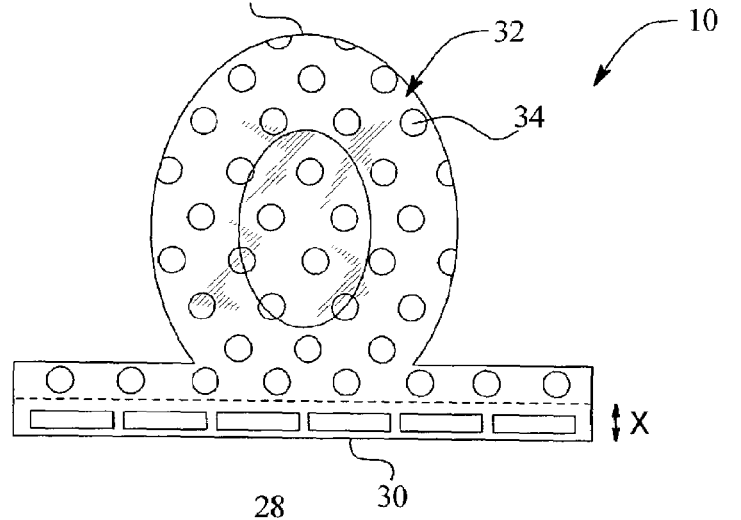
FIG. 3 is a bottom view of a dressing in an embodiment of the present invention.

Referring to FIG. 3, a bottom view of the dressing 10 without the liner 18 is generally illustrated. The top side 22 of the semi-permeable film 12 may be secured to the bottom 19 of the foam layer 11 from a top edge 28 of the base 23 of the foam layer 11 to a distance "X" from a bottom edge 30 of the wing 25. The first adhesive layer 16 coated on the bottom 19 of the foam layer 11 may be exposed from the bottom edge 30 of the dressing 10 to the distance "X" from the bottom edge 30. Further, the second adhesive layer 16 may have a stronger bond to the skin of a patient than the first adhesive layer 14. Alternatively, the top side 22 of the semi-permeable film 12 may be continuously secured to the bottom 19 of the foam layer 11 from a top edge 28 of the base 23 of the foam layer 11 to the bottom edge 30 of the wing 25.

The second adhesive layer 16 exposed on the wing 25 may have a stronger bond to the skin of a patient than the first adhesive layer 14. The second adhesive layer 16 may have properties that allow a stronger bond to the catheter and/or skin of a patient than the first adhesive layer 14. Accordingly, the wing 25 of the dressing 10 with the second adhesive layer 16 may be used to secure the dressing and/or catheter with minimal contact to the skin of the patient and the first adhesive layer 14 may be use to secure the dressing 10 to the skin of the patient.

Alternatively, the properties of the second adhesive layer 16 may be the same as the properties of the first adhesive layer 14. However, the second adhesive layer 16 may have a thickness of, such as, for example, one and a half (1.5) millimeters whereas a thickness of the first adhesive layer 14 may be one (1) millimeter. A thicker adhesive layer may provide a stronger bond. Preferably, the thickness of the second adhesive layer 16 and the first adhesive layer 14 may vary from 0.1 mm to 2.5 mm.

Figure 4:
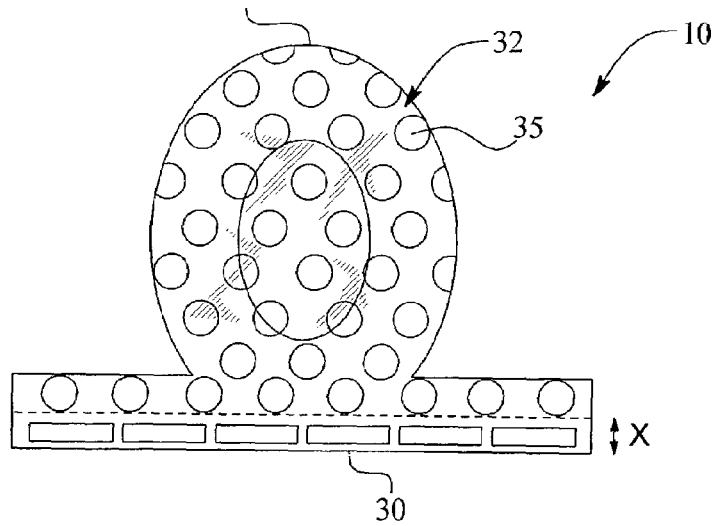
FIG. 4 is a bottom view of a dressing in an embodiment of the present invention.

Further, the first adhesive layer 14 may have a pattern 32 which may vary to allow more vapor transmission. For example, the pattern 32 may have a series of circles 34. In another embodiment, as illustrated in FIG. 4, the pattern 32 may have circles 35 wherein the circles 35 may have a diameter that is larger than the circles 34 as illustrated. The circles 34 may not cover as great of a surface area of the semi-permeable film 12 as the circles 35 and accordingly the circles 34 may allow for more vapor transmission in the semi-permeable film 12 than the circles 35. Of course, the pattern 32 is not limited to having circles and may have, for example, squares, or any other shape. Alternatively, the first adhesive layer 14 may not have a pattern and may be continuously and substantially evenly coated on the foam layer 11.

Figure 1F:
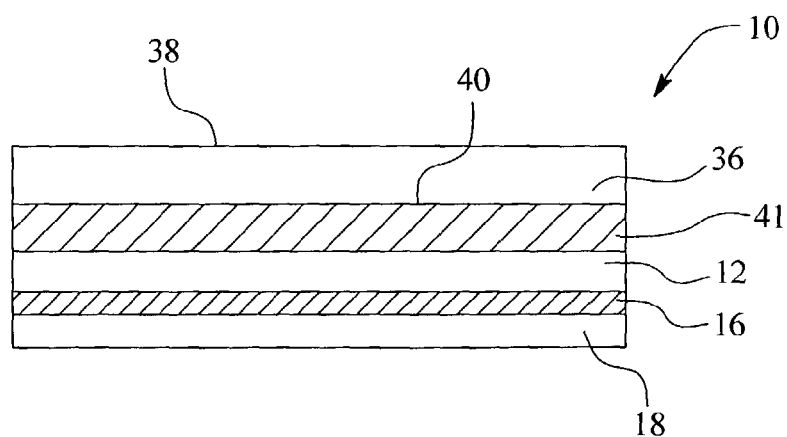
FIG. 1f is a cross-sectional view of a dressing taken generally along the line E—E of FIG. 2 in another embodiment of the present invention.

Referring to FIGS. 1*f* and 2, in an embodiment of the present invention, the dressing 10 may have additional foam pieces 36. The foam pieces 36 may have a top 38 and a bottom 40. The foam pieces 36 may be coated on the bottom 40 with an adhesive 41. The liner 18 may be removably attached to the adhesive 41 on the bottom 40 of the foam pieces 36. The foam pieces 36 may be used to secure the catheter.

In an embodiment, a patient identification label and/or information label 42 may be laminated or otherwise removably attached to the foam layer 11, one of the foam pieces 36, and/or the liner 18. The information label 42 may be used for documentation purposes. The liner 18 may be coated with silicone to accommodate the information label 42 and the foam pieces 36. More specifically, the liner 18 may have a top side 45 and a back side 47. Silicone may be coated both on the top side 45 and the back side 47 of the liner 18. The silicone coating on the liner 18 may allow for easy removal of the information label 42, foam pieces 36, and base 23 of the dressing 10. For example, the information label 42 may be removed from the dressing 10 and applied to patient records or the like.

Figure 5:
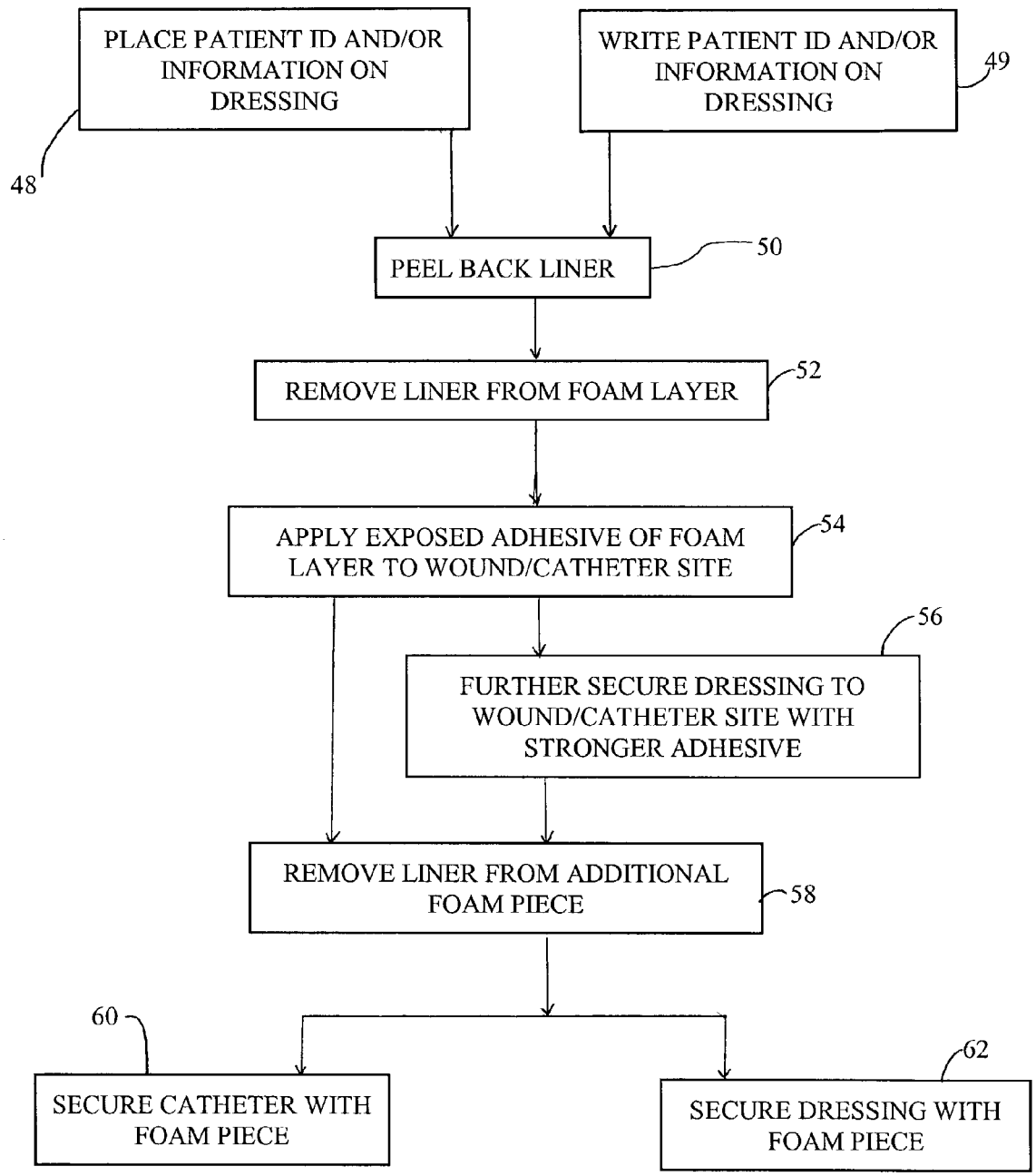
FIG. 5 is a flowchart illustrating applying a dressing to a patient in an embodiment of the present invention.

Referring to FIG. 5, a flowchart showing a method for applying the dressing 10 is generally illustrated. An individual may place a patient identification label and/or information label on the dressing 10 as shown at step 48. Alternatively, the individual may write information directly on the label as shown at step 49. The individual may skip step 48 and/or step 49 and may peel back the liner 18 as shown at step 50, to remove the same from the foam layer 11 of the dressing 10 as shown at step 52. After removal of the liner 18 from the foam layer 11, the individual may apply the exposed first adhesive layer 14 and the second adhesive layer 16 of the semi-permeable film 12 to the wound and/or catheter site of a patient as shown at step 54. The second adhesive layer 16 may have a strength greater than the first adhesive layer 14. The second adhesive layer 16 may have a greater strength to further secure the dressing 10 on the skin of the patient remote from the wound and/or catheter insertion site as shown at step 56.

The individual may further remove the liner 18 from one of the foam pieces 36 as shown at step 58. After removal of the liner 18 from one of the foam pieces 36, the one of the foam pieces 36 may be placed over the catheter to further secure the catheter and the dressing 10 as shown at step 60. Alternatively, one of the foam pieces 36 may be placed on the dressing 10 to further secure the dressing 10 as shown at step 62. Of course, the dressing 10 may be applied by the patient rather than by another individual.

Figure 6:
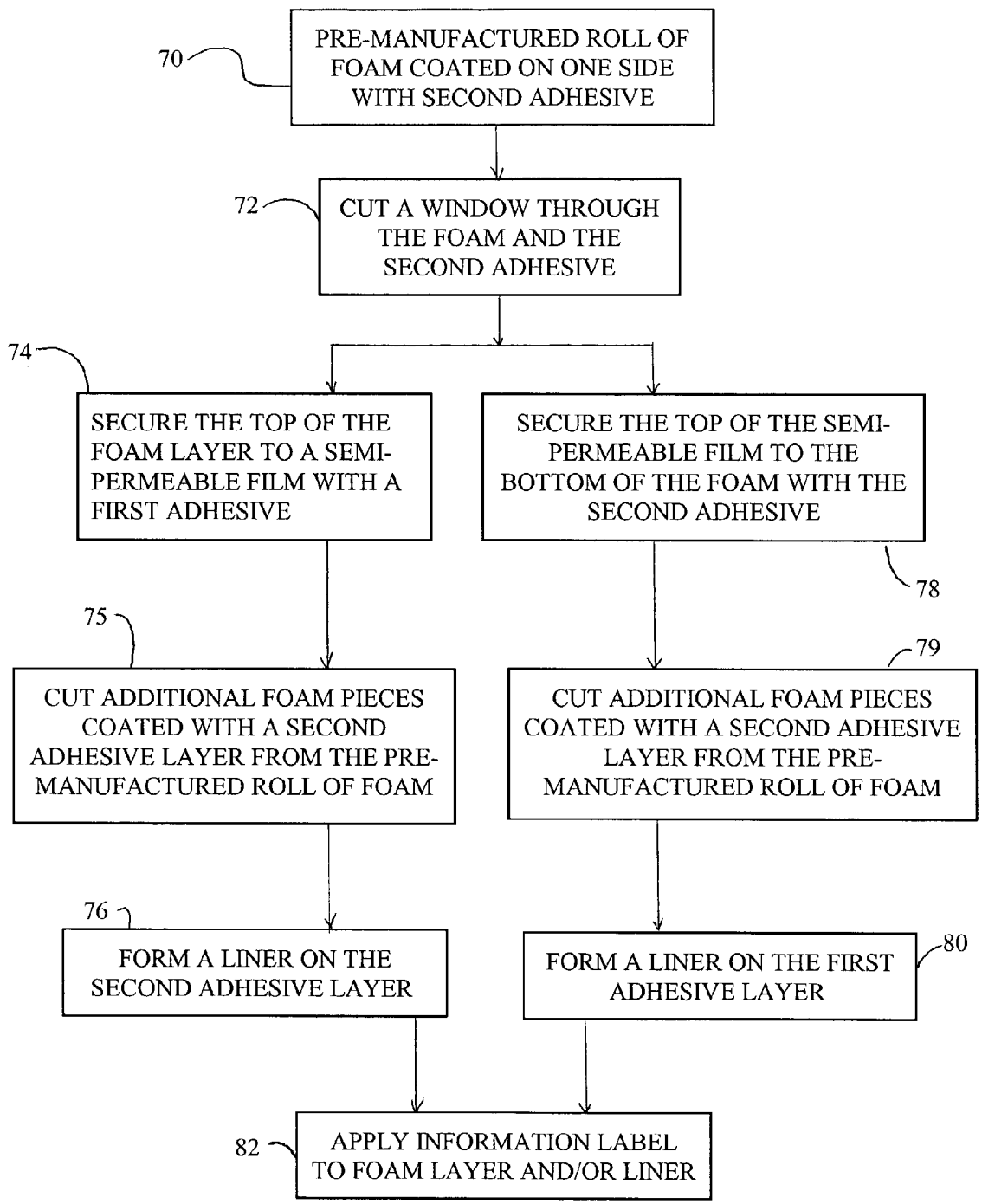
FIG. 6 is a flowchart illustrating the steps for making a dressing in an embodiment of the present invention.

A flowchart illustrating an embodiment of a method to manufacture the dressing 10 of the present invention is generally illustrated in FIG. 6. A pre-manufactured roll of the foam layer 11 with the second adhesive layer 16 substantially covering the bottom 19 of the foam layer 11 may be used as shown at step 70. A window 32 may be cut through the foam layer 11 and the second adhesive layer 16 as shown at step 72. A pre-manufactured roll of the semi-permeable film 12 with the first adhesive layer 14 substantially covering the bottom side 20 of the semi-permeable film 12 may be secured to the foam layer 11. The top 21 of the foam layer 11 may be secured to the semi-permeable film 12 by the first adhesive layer 14 as shown at step 74.

Additional foam pieces 36 with the second adhesive layer 16 remote from the base 23 of the foam layer 11 may be cut from the pre-manufactured roll of the foam layer 11 as shown at step 75. The liner 18, coated with silicone, may be formed on the second adhesive layer 16 as shown at step 76. Alternatively, the top side 22 of the semi-permeable film 12 may be secured to the bottom 19 of the foam layer 11 by the second adhesive layer 16 as shown at step 78 and additional foam pieces may be cut from the foam as shown at step 79. The liner 18 may be formed on the first adhesive layer as shown at step 80. The information label 42 may be applied to the liner 18 or alternatively to the foam layer 11 as shown at step 82.

It should be appreciated that the dressing 10 may be any number of shapes and/or sizes including rectangles, circles, triangles, and the like. Further, the dressing 10 may be any number of different colors. The different sizes, shapes, and/or colors may indicate the strength of the adhesive. For example, a dressing 10, in the color pink, may indicate a dressing 10 with the second adhesive layer 16 and/or the first adhesive layer 14 gentle enough to apply to a newborn, a baby, an infant or a child. The dressing 10, in the color blue, may indicate the dressing 10 with the second adhesive layer 16 and/or the first adhesive layer 14 of sufficient bonding strength to maintain adherence to a young adult. The dressing 10, in the color white, may indicate the dressing 10 with the second adhesive layer 16 and/or the first adhesive layer 14 that may be used with an adult or infant.

Further, the various shapes of the dressing 10, such as, for example, squares, ovals, or the like, may also be used to indicate the strength of the adhesive and/or to accommodate various shaped wounds and/or various sized catheters. Still further, the different sized dressings may be used for different sized wounds and/or different sized catheters.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A method for applying one of a plurality of dressings to a patient, each one of the plurality of dressings having a layer, a color associated with the layer, a semipermeable film, an adhesive and a liner, the method comprising the steps of:

choosing a dressing based on the color associated with the layer wherein the color indicates an adhesive strength of the adhesive;

providing a piece of foam removably attached to the liner;

exposing the dressing by removing the liner;

placing the exposed portion of the dressing on the patient such that the adhesive adheres to the patient; and securing the dressing on the patient with the piece of foam.

2. The method of claim 1 further comprising the steps of:

providing a label on the dressing; and writing information on the label.

3. The method of claim 2 further comprising the step of:

removing the label from the dressing.

4. A dressing comprising:

a semi-permeable film having a top side and a bottom side;

a layer having a top side and a bottom side secured to the top side of the semipermeable film;

a window in the layer wherein the window forms an opening extending through the layer from the top side to the bottom side of the layer;

a first adhesive having a first adhesive strength wherein the first adhesive is on the bottom side of the semipermeable film;

a second adhesive having a second adhesive strength wherein the second adhesive is on the bottom side of the layer and further wherein the first adhesive strength is greater than the second adhesive strength; and a color associated with the layer wherein the color is indicative of the adhesive strength of the second adhesive.

* * * * *